(12) United States Patent
Yoo et al.

(10) Patent No.: US 8,828,411 B2
(45) Date of Patent: Sep. 9, 2014

(54) DOSAGE FORMS AND METHODS OF USE THEREOF

(75) Inventors: Jae D. Yoo, East Windsor, NJ (US); Henry L. Surprenant, Phoenixville, PA (US); Donald C. Monkhouse, Radnor, PA (US); Thomas G. West, Lawrenceville, NJ (US)

(73) Assignee: Aprecia Pharmaceuticals Company, Langhorne, PA (US)

( * ) Notice: Subject to any disclaimer, the term of this patent is extended or adjusted under 35 U.S.C. 154(b) by 2010 days.

(21) Appl. No.: 11/750,887

(22) Filed: May 18, 2007

(65) Prior Publication Data

US 2007/0259010 A1    Nov. 8, 2007

Related U.S. Application Data

(63) Continuation of application No. PCT/US2005/042802, filed on Nov. 23, 2005.

(60) Provisional application No. 60/631,252, filed on Nov. 26, 2004.

(51) Int. Cl.
*A61K 9/00* (2006.01)
*A61K 9/20* (2006.01)

(52) U.S. Cl.
CPC .............. *A61K 9/2072* (2013.01); *A61K 9/2095* (2013.01)
USPC ........................................................ 424/400

(58) Field of Classification Search
CPC .................................................... A61K 9/2095
USPC ........................................................ 424/400
See application file for complete search history.

(56) References Cited

U.S. PATENT DOCUMENTS

| | | | | |
|---|---|---|---|---|
| 3,015,609 | A * | 1/1962 | Sanders, Jr. | 424/10.2 |
| 6,799,725 | B1 | 10/2004 | Hess et al. | |
| 7,276,252 | B2 * | 10/2007 | Payumo et al. | 424/472 |
| 2003/0039691 | A1 | 2/2003 | Waterman | |
| 2003/0143268 | A1 * | 7/2003 | Pryce Lewis et al. | 424/464 |
| 2004/0166063 | A1 | 8/2004 | Siegel | |

OTHER PUBLICATIONS

Katstra et al., Oral Dosage Forms Fabricated by Three Dimensional Printing, Journal of Controlled Release 66 (2000) 1-9.
Rowe et al., Multimechanism Oral Dosage Forms Fabricated by Three Dimensional Printing, Journal of Controlled Release 66 (2000) 11-17.
Wu et al., Solid Free-Form Fabrication of Drug Delivery Devices, Journal of Controlled Release 40 (1996) 77-87.
Wang et al., Development of Near Zero-Order Release Dosage Forms Using Three Dimensional Printing (3DP) Technology. Drug Development and Industrial Pharmacy 32: 367-376, 2006.
Lee et al., Evaluation of Critical Formulation Factors in the Development of a Rapidly Dispersing Captopril Oral Dosage Form. Drug Development and Industrial Pharmacy vol. 29, No. 9, pp. 967-979, 2003.

* cited by examiner

*Primary Examiner* — Jake Vu
(74) *Attorney, Agent, or Firm* — Rick Matos; Innovar, L.L.C.

(57) ABSTRACT

Pharmaceutical dosage forms with external or internal features to complicate counterfeiting and support authentication are described. External features include surface texture, surface markings defined by patterns of physical or chemical markers, or complex interlocking shapes. Internal features also include physical or chemical markers in two or three-dimensional patterns observable after sectioning, or after breaking along designed fracture lines. Methods of manufacture using solid freeform fabrication (SFF) techniques such as three-dimensional printing (3DP) are described. Method of authentication using dosage form patterns and batch codes are also described.

22 Claims, 4 Drawing Sheets

DOSAGE FORMS AND METHODS OF USE THEREOF

1. CROSS-REFERENCE TO EARLIER FILED APPLICATIONS

The present application is a CONTINUATION of and claims the priority of PCT International Application No. PCT/US05/42802 filed Nov. 23, 2005, and of U.S. Provisional Application No. 60/631,252 filed Nov. 26, 2004, the entire disclosures of which are hereby incorporated by reference.

2. FIELD OF THE INVENTION

This invention relates generally to dosage forms and production methods in the pharmaceutical arts, and more specifically to solid dosage form designs and strategies that may be used to complicate or defeat efforts at counterfeiting.

3. BACKGROUND OF THE INVENTION

Conventional pharmaceutical dosage forms are well known and ubiquitous in the treatment of disease. This category includes the familiar pills, tablets, capsules, caplets, gel-caps, and other solid dosage forms that comprise the vast majority of pharmaceutical products on the market today.

However, not all of the products sold today are authentic. In recent years, there has been a significant increase in the number of false or counterfeit pharmaceutical goods in the marketplace. Direct-to-consumer marketing, global price competition, and Internet sales have all increased the likelihood that counterfeit pharmaceuticals may be produced or consumed anywhere in the world. It has been estimated that 10% of the pharmaceutical products sold globally are counterfeit, with substantially higher incidence among expensive medications or medications in high demand. (World Health Organization Fact Sheet No. 275, November 2003)

These counterfeit products generally imitate the external characteristics of the original products, such as size, shape, weight, color, or the presence of text or logos on the surface, using the same basic process technology as the originals. The resulting counterfeit pharmaceuticals may range from poor imitations with no active ingredient to products that contain related actives or wrong amounts of the correct active.

Efforts to defeat pharmaceutical counterfeiting thus far have focused on two main approaches. The first is the use of chemical markers or "taggants" in the dosage form that could be detected using sophisticated analytical techniques. The second is the use of radio frequency identification (RFID) technology on the product packaging to track and authenticate its identity throughout the supply chain, generating a "pedigree" for each product. (FDA Report, "Combating Counterfeit Drugs", Feb. 18, 2004).

While these approaches hold promise in reducing the incidence of counterfeiting, they have foreseeable limitations. The chemical marker approach may be defeated by discovering the identity of the marker (through chemical analysis or other means) and adding it to counterfeit dosage forms. This is particularly true when the marker is added throughout the dosage forms, or uniformly to the surface of the dosage form, using common pharmaceutical processing techniques. Similarly, the RFID approach may be defeated by using electronic means to change or falsify the reading, transmission, or content of the electronic "pedigree". Moreover, RFID techniques are not tied directly to the physical dosage forms, i.e.—a counterfeit product could exist within a package with proper RFID. Finally, these two strategies require the use of specific equipment or information to verify product identity. While they may work well for government and industry professionals along the supply chain, they do not offer any means of direct verification for the patient who ultimately uses the medication.

Hence, there is a need for additional dosage form attributes and related strategies that may further improve the ability to authenticate pharmaceutical products and deter counterfeiting efforts. Furthermore, it may be desirable that such strategies incorporate features that can be identified by the end user, the patient.

One approach to impart new attributes to pharmaceutical dosage forms is to use new process technology in their manufacture. Among the technologies that hold promise in this respect are the solid freeform fabrication (SFF) techniques, which use a layer-by-layer process sequence to assemble three-dimensional structures. These processes can create complex internal and external geometries by creating a different pattern as each "slice" of the structure is added.

One SFF process, three-dimensional printing (3DP), has particular utility for the creation of pharmaceutical dosage forms based on its ability to handle most active and inactive pharmaceutical ingredients. Although a variety of pharmaceutical dosage forms by 3DP have been disclosed in the art, no reference has been made to the problem of pharmaceutical counterfeiting or to structures or strategies that may serve to reduce or inhibit efforts at counterfeiting.

4. SUMMARY OF THE INVENTION

The invention encompasses dosage forms for the pharmaceutical or nutraceutical industry that can be used either individually or in combination in an effort to deter counterfeiting, to provide tamper resistance, or to provide safer preparations of a pharmaceutical or nutraceutical dosage forms. Other embodiments may also exist within the scope and spirit of the invention, as will be recognized by those skilled in the art.

In one embodiment, the invention encompasses dosage forms with unique external characteristics that are difficult to replicate. Such characteristics include, without limitation, the size, shape, weight, or color of the dosage form, or the presence of text, logos, or other markings on the surface. In one embodiment, the surface of the dosage form may include a uniform, regular texture that may be used to identify it. In another embodiment, the dosage form may have surface markings that may be defined by specific regions with raised or lowered surface features, or may be defined by patterns of color, chemical markers, or combinations thereof. These patterns may be readily observable, or may require exposure to chemicals or common substances for observation, or may require use of analytical equipment for detection, or combinations thereof. In still another embodiment, the dosage form may comprise an unusual overall structure such as "ball-in-cage," "chain links," "intersecting spheres," or other complex form that may be difficult to replicate. In yet another embodiment, the dosage form may be fabricated in the same process, and with the same materials, as a packaging-like enclosure, resulting in a structure-within-a-structure.

Another embodiment of the invention encompasses dosage forms with unique internal characteristics that may be difficult to replicate. In one embodiment, two- or three-dimensional patterns may be incorporated within the dosage forms by specific placement of dyes or other physical or chemical markers. These patterns may extend globally throughout the device, or may be confined to specific regions of the device, or combinations thereof. Upon breaking or sectioning the dosage form, these patterns may be readily observable, or may require exposure to chemicals or common substances for observation, or may require use of analytical equipment for detection, or combinations thereof. Multiple patterns may be observable by breaking or sectioning the dosage form in different ways. In one variation, the dosage forms may be designed to break in one or more predetermined ways to expose internal patterns used for authentication. In another variation, the patterns may lie just below the outer surface of the dosage form, and thus may be observable in whole or in part through said outer surface. In still another variation, there may be regions of loose powder within a dosage form.

In another embodiment, the invention encompasses the use of solid freeform fabrication (SFF) techniques to make dosage forms that are difficult to counterfeit. In one embodiment, the SFF technique used may be three-dimensional printing (3DP). The SFF technique may also be used in conjunction with other processing steps. In one embodiment, a dosage form intermediate is created using 3DP and undergoes subsequent compression. In one variation of this embodiment, the dosage form produced may have an internal pattern that is concealed on the dosage form intermediate from 3DP and is revealed on the final dosage form following compression. One or more other conventional processing techniques, such as surface coating and conventional surface finishing and printing, may also be used in combination with an SFF technique to produce dosage forms in accordance with the present invention.

Still another aspect of the present invention includes a method of authenticating dosage forms. In one embodiment, this method includes the matching of an internal or external pattern, such as those described above, to a reference standard. The standard may be provided in the package insert or may be accessible via secure Internet connection or other means. In a related embodiment, the method may require input of information into a web-based form, such as one or more product codes from the primary package, and selection of one or more internal or external patterns from the dosage form based on a list of many available patterns on the form. The product codes or internal or external patterns may be derived randomly from much larger pool of available options, with a low percentage of the total combinations in use at any one time.

5. BRIEF DESCRIPTION OF THE DRAWINGS

The present invention will be better understood by examining the following figures which illustrate certain properties of the present invention wherein.

6. DETAILED DESCRIPTION OF THE INVENTION

6.1. General

The invention encompasses a dosage form comprising:
(a) at least one active ingredient and at least one inactive ingredient; and
(b) one or more chemical markers,
wherein said one or more chemical markers define one or more patterns that may be used to authenticate the dosage form.

In one embodiment, the one or more patterns of the dosage form are internal patterns. In another embodiment, the one or more patterns of the dosage form are external patterns. In another embodiment, the internal patterns are three-dimensional patterns. In another embodiment, the internal patterns are two-dimensional patterns. In another embodiment, the external patterns are three-dimensional patterns. In another embodiment, the external patterns are two-dimensional patterns.

Another embodiment encompasses, the dosage form comprising one or more additional chemical markers. In another embodiment, the one or more additional chemical markers define one or more external patterns. In yet another embodiment, the one or more additional chemical markers define one or more internal patterns.

In another embodiment, the dosage form encompasses one or more fracture lines. In another embodiment, the one or more fracture lines to facilitate exposure of said one or more patterns. In another embodiment, the one or more patterns are internal patterns.

In another embodiment, the dosage form encompasses a uniform surface texture in the size range of 50-1000 microns.

In another embodiment, the dosage form encompasses one or more interlocking pieces. In another embodiment, the one or more interlocking pieces comprise a ball-in-cage structure.

In another embodiment, the dosage form encompasses one or more chemical markers are chosen from the group consisting of dyes, pigments, color-shift substances, UV-active substances, fluorescent substances, active pharmaceutical ingredients, and inactive pharmaceutical ingredients.

In another embodiment, the one or more chemical markers are imperceptible to the naked eye. In another embodiment, the one or more chemical markers may be revealed through reaction with a household substance.

In another embodiment, the one or more internal patterns may be detected just below the outer surface of the dosage form. In another embodiment, the dosage form is fabricated by three-dimensional printing.

In another embodiment, at least one active ingredient and/or at least one inactive ingredient are in a solid matrix.

In another embodiment, the dosage form encompasses two-dimensional patterens wherein at least one pattern comprises lettering, numbering, a dot pattern, or a bar code.

In another embodiment the dosage form is counterfeit-resistant. In another embodiment, the dosage form is tamper-resistant.

Another embodiment of the invention encompasses a dosage form comprising:

(a) an outer structure comprising a rapidly-dispersing solid matrix; and
(b) an inner structure comprising a solid matrix comprising at least one active ingredient and at least one inactive ingredient;
(c) one or more chemical markers, wherein said dosage form is suitable for swallowing upon dispersion of said outer structure.

In one embodiment, the outer structure further comprises at least one active ingredient.

Another embodiment encompasses a method for authenticating the dosage form of the invention comprising matching one or more patterns to one or more reference standards.

Another embodiment encompasses one or more reference standards are provided by packaging, package insert, or secure Internet connection. In another embodiment, at least one pattern is chosen randomly from a large pool of pattern combinations such that the total number of patterns in use is much smaller than those not in use from the pool. In another embodiment, at least one pattern is imperceptible by the naked eye. In another embodiment, one or more patterns includes numbering. In another embodiment, the numbering may be separated into individual digits for subsequent addition to obtain a secondary values for comparison to reference standards.

6.2. Dosage Forms of the Invention

The invention encompasses solid pharmaceutical dosage forms with external or internal features, or combinations thereof, that make difficult any efforts to copy, mimic, or otherwise counterfeit the dosage form. Those skilled in the art will recognize that such features may be incorporated into dosage forms of all types and applications, including oral, implantable, or other routes of delivery, and immediate, controlled, or other types of release. Similarly, the materials used in the practice of the invention may include the full scope of materials commonly employed in the pharmaceutical arts. A sample listing of such materials may be found in the Handbook of Pharmaceutical Excipients, Fourth Edition (Eds. R Rowe, P Shesky, P Weller, Pharmaceutical Press, 2003). Additional aspects of the present invention are directed toward methods of manufacture and methods of authentication for said dosage forms.

Solid freeform fabrication (SFF) techniques may be used for producing the dosage forms described in the present invention. Examples of SFF techniques include ballistic particle manufacturing, described in U.S. Pat. No. 5,633,021, fused deposition modeling, described in U.S. Pat. Nos. 5,260,009 and 5,503,785, and three-dimensional printing (3DP), among others. These patents are hereby incorporated by reference.

The basic process of 3DP is described in U.S. Pat. Nos. 5,204,055; 5,340,656; and 5,387,380. Additional U.S. patents and applications related to 3DP cover the following: preparation of medical devices (U.S. Pat. Nos. 5,490,962; 5,518,690; 5,869,170; 6,530,958), multi-phasic dosage forms (U.S. Pat. Nos. 6,280,771; 6,514,518), rapidly dispersing dosage forms (U.S. Pat. No. 6,471,992), encapsulation of toxic materials in dosage forms (2002/0015728), methods for controlling binder migration (2002/0106412), uniaxial compression of dosage forms (2003/0143268), dosage forms exhibiting zero-order release (2003/0198677), suspension printing (2003/0198677), and diffusion controlled dosage forms (2004/0005360). The disclosure of each of these documents is hereby incorporated by reference.

For a detailed description of 3DP, reference can be made to a number of the patents and applications listed above. Briefly, three-dimensional printing creates structures through a repeated sequence of spreading thin layers of loose powder and binding areas within the layers by selective deposition ("printing") of a fluid material. The process continues, building vertically layer-by-layer, until a full three-dimensional structure or group of structures is created. Areas where fluid droplets are deposited become solid regions, and areas where no fluid droplets are deposited remain as loose powder. After the parts are printed and dried, the solid parts may be separated from the loose powder. Because the pattern printed on each layer can be different, the structures resulting from 3DP can have complex internal and external characteristics, unlike those of conventional manufacturing techniques. Multiple nozzles may be used in 3DP to deposit multiple fluid materials within the structures. Hence, the process lends itself to local control of both geometry and composition.

The manufacturing instructions for a print job may be generated a variety of ways, including direct coding, derivation from a solid CAD model, or other means specific to the 3DP machine's computer interface and application software. These instructions may include information on the number and spatial placement of droplets, and on general print parameters such as the drop spacing in each linear dimension (X, Y, Z), and volume or mass of fluid per droplet. For a given set of materials, these parameters may be adjusted in order to refine the quality of structure created. The overall resolution of the structure created is a function of the powder particle size, the fluid droplet size, the droplet-powder ballistics, the print parameters, and the material properties.

In terms of materials, the powder may comprise a single material or a blend of materials to achieve the desired properties. One or more fluids for binding may be used, and may include pure solvents, solutions, suspensions, or other fluid media suitable to bind the powder layers. For pharmaceutical dosage forms, these materials may be chosen from those commonly used in the pharmaceutical arts, including those listed in the Pharmaceutical Excipients Handbook referenced above, and other materials such as active ingredients that are appropriate for such products. Both active and inactive ingredients may be incorporated via the powder or fluid route, or both, although the fluid route is often preferred for the active ingredients based on material efficiency and control of placement.

Because of its ability to handle a range of pharmaceutical materials and control both composition and architecture locally, 3DP is well suited to the fabrication of dosage forms that are difficult to counterfeit in accordance with the present invention.

In one aspect of the present invention, external features are created that may be used to identify, distinguish, or authenticate a genuine product from a counterfeit product. In one embodiment, the surface of the dosage form has a uniform texture that may be used to identify it.

Such a dosage form may be achieved by using 3DP, with the texture resulting from the resolution of the process. As mentioned above, the overall resolution of the structure created is a function of the powder particle size, the fluid droplet size, the droplet-powder ballistics, the print parameters (X, Y, Z drop spacings), and the material properties. Of these factors, the layer thickness (i.e. —drop spacing in the Z direction) may be the most dominant parameter, although other factors may be used. Generally speaking, the layer thickness in a print job must be larger than the particle size of the powder used in order to facilitate spreading of the powder and prevent damage to the surface of the new layer or shifting of the underlying material. Hence, the layer thickness may range from about 50 to 1000 microns in size, preferably about 100 to 500 microns. Dosage forms produced using layer thickness in this range will tend to generate a laminar texture along the sides, usually evident to the naked eye. The texture is particularly evident along any curved surfaces on the top or bottom of the dosage form.

In general, dosage forms created using 3DP may exhibit multiple levels of texture that can be used to distinguish the dosage form from potential counterfeits. Using the naked eye, it may be possible to identify the texturing associated with any or all of the three drop spacings (X, Y, Z). Smaller elements of texture related to the powder particle size and resulting microstructure of the printed part may be discerned by using appropriate apparatus, e.g. an electron microscope. Using such an apparatus, it may be possible to observe a dosage form created by 3DP at sufficient magnification to see both the texture associated with the drop spacings (and drop size) and the texture associated with the powder particle size.

It should be noted that a given print job may not be limited to a single set of these parameters for the entire structure to be created. Any or all of the drop spacings may be varied in selected regions of the print job if desired. This approach may be desirable, for example, to improve the resolution in the top and bottom regions of a dosage form having curved surfaces, or for the fabrication of dosage forms using multiple powders or powder blends in different regions of the device. Other variations along this theme also exist, as may be appreciated by those skilled in the art. Other variations of laminar texturing may be achieved using other SFF processes, as will be recognized by those skilled in the art.

In another embodiment of the present invention, the dosage form may have text, logos, or other surface markings that may be defined by specific regions with raised or lowered surface features, or may be defined by patterns of color, chemical markers, or combinations thereof.

Using a process such as 3DP, raised or lowered regions may be created through the specific inclusion or exclusion of fluid drops in the pattern printed. This inclusion or exclusion of droplets may be handled in the initial programming of instructions for the 3DP apparatus, as described above. The resolution on such features depends upon a number of factors but is generally within the range of 50 to 1000 microns. Hence, the thickness of the line used in any text, logo, or other surface marking may lie within this range, and may thus be used to create either subtle or conspicuous features on the surface of a dosage form that may distinguish it from counterfeits.

Features of similar resolution may be created that incorporate coloring or chemical markers. This may be accomplished by printing the dosage forms using two or more fluids to bind the powder. In this case, the first fluid contains the chemical marker, and may be deposited specifically within a line pattern that constitutes the text, logos, or other surface marking desired. The second fluid contains either no chemical marker or a different chemical marker than the first fluid, and may be used to bind the remainder of the dosage form. A similar approach may be used with as many fluids and chemical markers as needed to achieve the desired effects of creating the dosage form and the surface features. Chemical markers in accordance with this approach may include dyes, pigments, color-shifting substances, UV active or fluorescent substances, active or inactive pharmaceutical ingredients, or any other appropriate chemical entity that can be distinguished from its surround materials using an appropriate technique. These features may be as simple as a pattern of dots or as intricate as a bar code pattern suitable for scanning.

Figure 1:
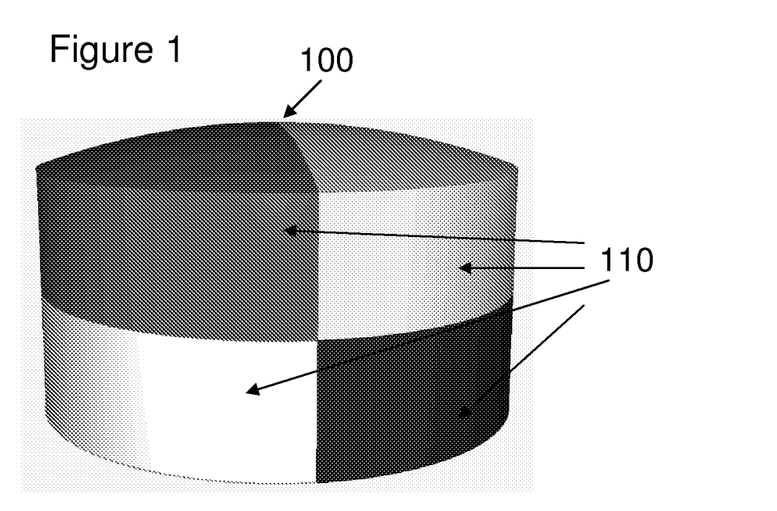
FIG. 1 is an isometric view and sectioned isometric view of a dosage form embodiment in accordance with two aspects of the present invention.

FIG. 1 illustrates a dosage form 100 with multiple regions 110 distinguished by use of different chemical markers. These markers are present on the outer surface of the dosage form as well as the interior, as shown on the cutaway view.

In accordance with the present invention, it may be desirable that the identifying features of the dosage forms become observable upon exposure to other substances as a result of physical or chemical change. Such change may include preferential dissolution of one material, or chemical reaction of a material to change properties such as color or spectroscopic signature, or any other such change that may increase or provide contrast between the identifying region and the surrounding areas of the dosage form. In one version of this embodiment, the substance that effects the change may be a fairly common household item the includes a desired chemical entity, including baking soda (sodium bicarbonate), vinegar (dilute acetic acid), hard liquor such as vodka (40% ethanol), rubbing alcohol (dilute isopropanol), milk (lactose, cream, milk protein), juice (citric acid, fructose), cooking oil, seltzer water (carbonic acid), sugar (sucrose), laundry bleach (sodium hypochlorite), milk of magnesia (magnesium hydroxide), or salt (sodium chloride). Additional household substances may also be of use as recognized in the chemical arts.

Techniques that may be used to discern the distinguishing features of the present invention include direct observation with the naked eye, optical microscopy, electron microscopy, micro-FTIR spectroscopy, micro-Raman spectroscopy, surface profilometry, or any other analytical technique capable of distinguishing physical or chemical differences at the resolution of the features described herein. It is contemplated that improvements in the resolution of the manufacturing process or analytical equipment may enable the use of distinguishing features of smaller size than that disclosed herein. Such improvements are considered to lie within the scope and spirit of the present invention.

In another embodiment of the present invention, the dosage form may comprise an unusual overall structure such as "ball-in-cage", "chain links", "intersecting spheres", or other complex form that may be difficult to replicate or counterfeit. Structures such as these may be made using an SFF process such as 3DP by inputting machine instructions with sufficient complexity, and choosing materials and print parameters with sufficient resolution to capture the complex form desired. As mentioned above, the machine instructions may be derived from a number of sources, including the conversion of a CAD drawing or other solid model. For 3DP, the matching of material sets and print parameters to achieve a particular resolution may proceed by systematic testing of the three droplet spacings (X, Y, Z) and the droplet volume to adjust the level of fluid saturation achieved locally in the powder. Such an approach is commonly known and used by those skilled in the art. In a related embodiment, the dosage form may be fabricated in the same process, and with similar materials, as a packaging-like enclosure, resulting in a structure-within-a-structure. It may be desirable to make such a structure via 3DP.

Figure 2:
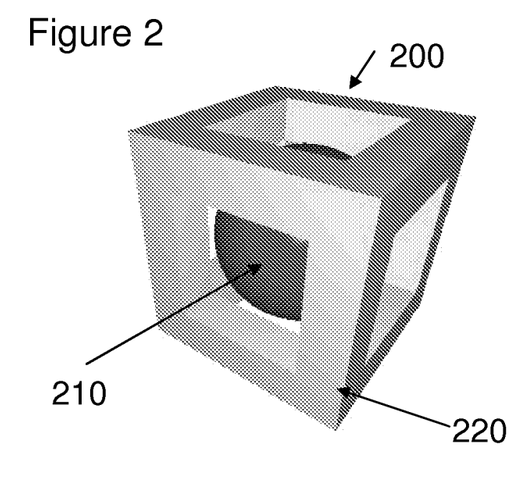
FIG. 2 is an isometric view of a "ball-in-cage" dosage form embodiment in accordance with one aspect of the present invention.
Figure 3:
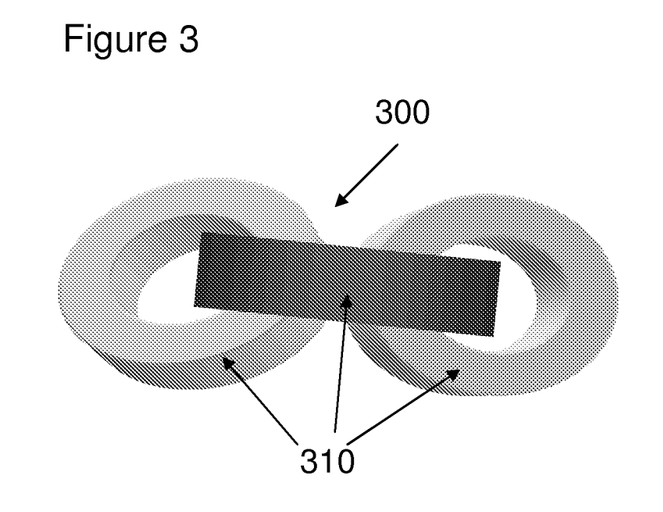
FIG. 3 is an isometric view of a "chain links" dosage form embodiment in accordance with one aspect of the present invention.
Figure 4:
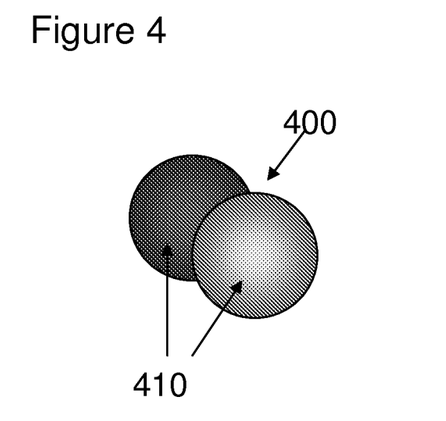
FIG. 4 is an isometric view of an "intersecting spheres" dosage form embodiment in accordance with one aspect of the present invention.
Figure 5:
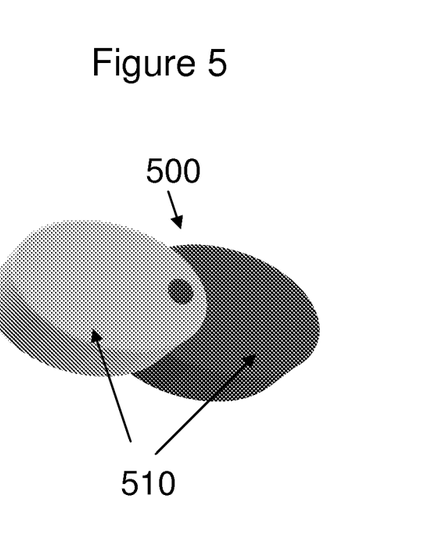
FIG. 5 is an isometric view of a segmented, interlocking dosage form in accordance with one aspect of the present invention.
Figure 6:
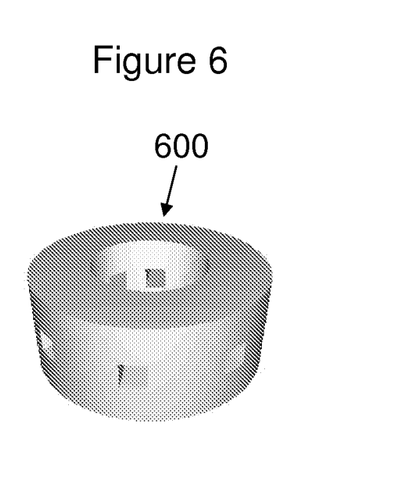
FIG. 6 is an isometric view of a cylindrical dosage form with axial channel and radial channels in accordance with one aspect of the present invention.

The "ball-in-cage" 200, "chain links" 300, and "intersecting spheres" 400 dosage forms are illustrated in FIGS. 2, 3, and 4, respectively. In FIG. 2, the ball 210 and the cage 220 are not attached, and are free to move independent of one another. Similarly, in FIG. 3, the chain links 310 may also move independently, and are unattached (although interlocking). In FIG. 4, the two spheres 410 are connected as a single, solid piece, as are the segments 510 of the dosage form 500 in FIG. 5. The ring-shaped dosage form 600 in FIG. 6 defines a single axial channel along with several intersecting radial channels.

Figure 7:
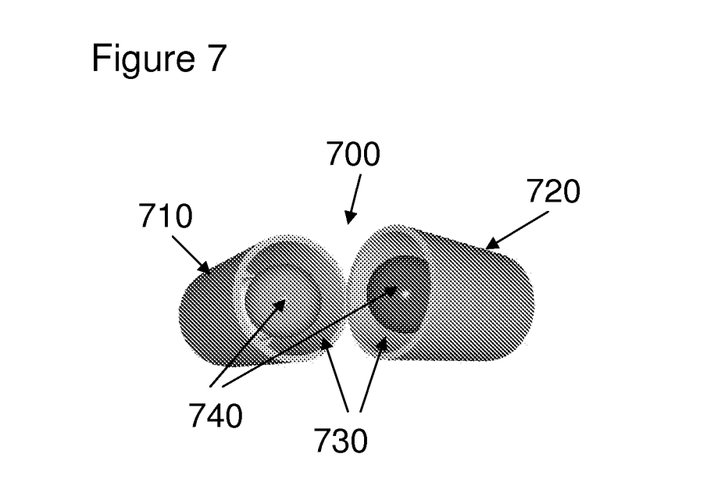
FIG. 7 is an isometric view of "structure-within-a-structure" dosage form in accordance with one aspect of the present invention.

FIG. 7 illustrates a dosage form 700 that comprises a structure-within-a-structure. In this case, the outer structure resembles the two pieces 710 and 720 of a capsule, and the interior is filled with both loose powder 730 and other spherical structures 740. Such a dosage form may be made directly by an SFF process such as 3DP.

Most conventional pharmaceutical dosage forms are designed to be easy for the patient to swallow. In general, these dosage forms have rounded surfaces, and no more than one long dimension (as in capsules, caplets, and gelcaps). The dosage forms disclosed herein, with unusual overall physical shapes, may be designed with this wisdom in mind. In accordance with the embodiment above, it may be desirable to create a dosage form with a shape that resembles a capsule, but includes channels that go through the device and are visible as holes on the surface. Similarly, it may be desirable to create a structure-within-a-structure in which the inner structure comprises a dosage form with shape suitable for swallowing, and the outer structure comprises a rapidly dispersing structure intended for dissolution in the mouth upon administration or outside the body (similar to "opening" a package). In the case of an entirely rapidly-dispersing dosage form, virtually any shape may be acceptable since the dosage form is not intended to be swallowed intact, and thus does not require rounded sides or particular dimensions.

Another aspect of the present invention provides for dosage forms with unique internal characteristics that may be difficult to replicate. In one embodiment, two- or three-dimensional patterns may be incorporated within the dosage forms by specific placement of dyes or other physical or chemical markers. These patterns are distinct from the surface features and markings described above in that they are internal to the dosage form, and cannot be fully observed with the dosage form intact. Moreover, they may extend more fully into the volume space of the of the dosage form, and may constitute complex three-dimensional arrangements that are non-concentric, asymmetric, or otherwise locally variable.

These patterns may extend globally throughout the device, or may be confined to specific regions of the dosage forms, or combinations thereof. Upon breaking or sectioning the dosage forms, these patterns may be readily observable, or may require exposure to chemicals or common substances for observation, or may require use of analytical equipment for detection, or combinations thereof. Multiple patterns may be observable by breaking or sectioning the dosage forms in different ways. Three-dimensional patterns may be designed to expose pre-specified two-dimensional patterns on the exposed interior surfaces of the dosage forms when the dosage forms broken or cut along specific axes of the dosage forms.

Using a process such as 3DP, multiple fluids may be deposited in pre-selected regions within a device to create internal patterns or features in accordance with this embodiment. As described above, one or more of these fluids may contain the desired markers and may be used to print a pattern of droplets suitable for identification purposes and pre-defined in the machine instructions. The chemical substances chosen and the analytical techniques that may be applicable are similar to those described above for external features and markings. Also as described above, these features may have resolution in the range of 50-1000 microns, and may be as simple as a pattern of dots or as intricate as a bar code pattern. Such features may be readily observable, or may require exposure the chemical substances, including household items. The use of smaller features relying on printing technology and analytical equipment with higher resolution than that presently available is considered to lie within the scope of the present disclosure.

In one variation of this embodiment, the dosage forms may be designed to break in one or more predetermined ways to expose internal patterns used for authentication. Using 3DP, such dosage forms may be created by designing a larger gap between droplets, or removing droplets entirely, or other modifications in structure or composition, along the designed fracture line. As in the case of the features described above, the details of the fracture lines may be defined in the initial set of machine instructions used to create the dosage forms. The identification of specific parameters for an effective fracture line may be achieved through iteration. In the case of wider spacing for droplets along the fracture line, testing may proceed by using multiples of the normal drop spacing until the desired properties are achieved. In the case of exclusion of droplets, testing may proceed by removing droplets in increasing frequency along the desired fracture line, e.g. not printing one out of five, or one out of four, or one out of three of the droplets that would normally be printed therein. Other approaches or methodologies may also be used to achieve the desired results, as recognized by those skilled in the art.

In a related embodiment, an internal pattern may be created that lies just below the external surface of the dosage form in such a way as to allow the observation of the pattern through the external surface. In one variation of this embodiment, the dosage form may be created through an initial SFF step such as 3DP and a subsequent processing step such as compression. In this variation, the internal pattern may not be observable on the dosage form intermediate resulting from the SFF process, but may then become observable on the final dosage form resulting from compression.

Some examples of internal patterns and structures have been mentioned above. In FIG. 1, the external pattern of chemical markers 110 shown also reflects the internal pattern of the dosage form. In FIGS. 2, 3, and 7, physical structures are created that are internal to one another.

Figure 8:
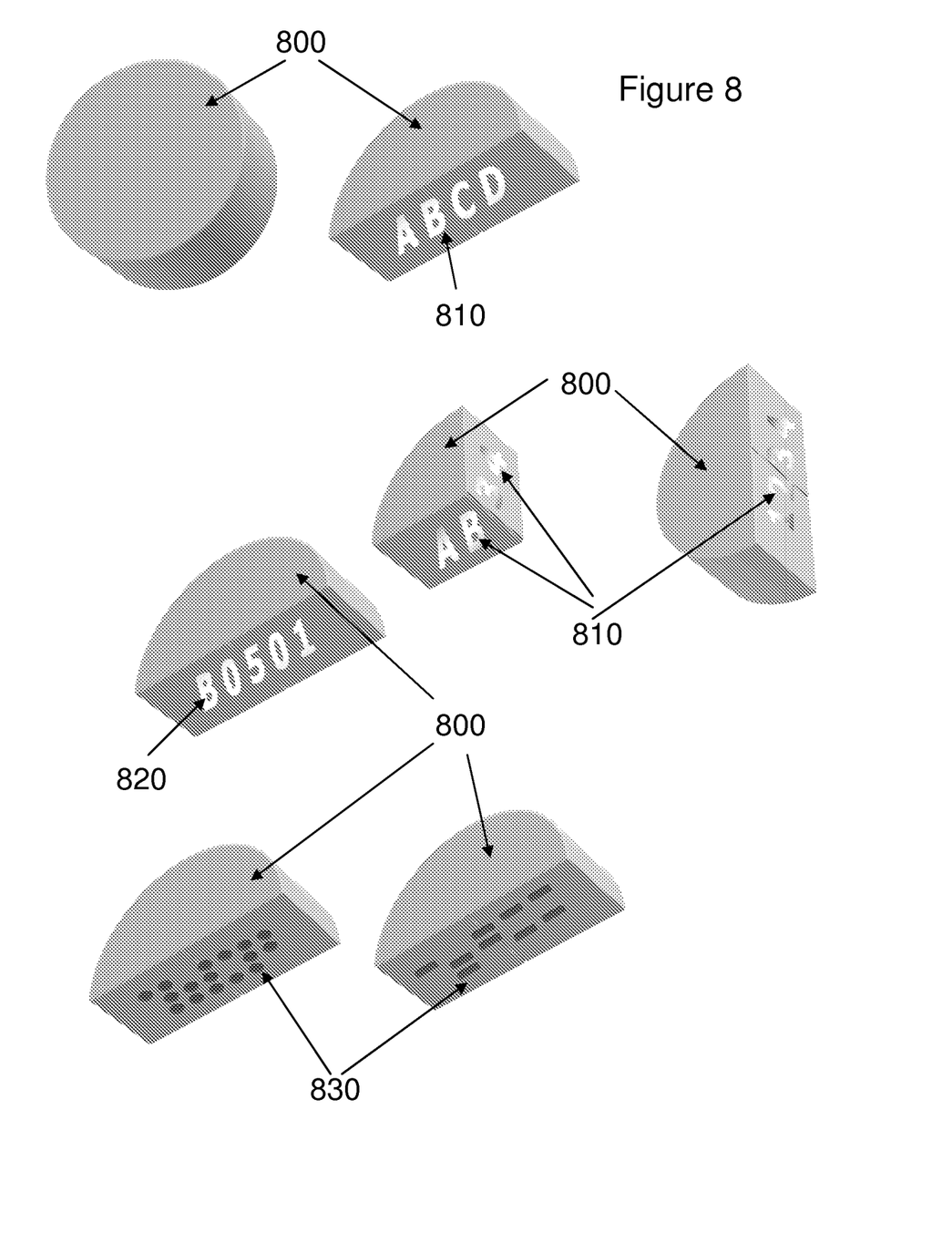
FIG. 8 includes an isometric view and multiple isometric sections of dosage form embodiments in accordance with one aspect of the present invention.

FIG. 8 contains multiple views of a dosage form 800 with internal patterns that may be viewed by breaking or sectioning the dosage form 800. These patterns include letters and numbers that lie along different axes 810 of the same dosage form, batch codes 820, and other internal patterns 830 that may be used for identification.

Yet another aspect of the present invention includes the use of solid freeform fabrication (SFF) techniques to make the dosage forms that are difficult to counterfeit. In a preferred embodiment, the SFF technique used may be three-dimensional printing (3DP). Although the examples of this disclosure are mostly described in terms of three-dimensional printing, other SFF techniques may be used in accordance with the knowledge of the respective processing art. For such SFF processes, the ability to change and rapidly prototype a new version of a dosage form is considered advantageous in the effort to combat pharmaceutical counterfeiting. Similarly, the ability to combine one or more SFF techniques with more traditional processes such as compression, coating, and surface finishing or printing, is also advantageous in the creation of dosage forms with multiple features that may be used for authentication.

Still another aspect of the present invention includes a method of authenticating dosage forms. In one embodiment, this method includes the matching of an internal or external pattern, such as those described above, to a reference standard. The standard may be provided in the package insert or may be accessible via secure Internet connection or other means. In a related embodiment, the method may require input of information into a web-based form, such as one or more product codes from the primary package, and selection of one or more internal or external patterns from the dosage form based on a list of many available patterns on the form. The product codes or internal or external patterns may be derived randomly from much larger pool of available options, with a low percentage of the total combinations in use at any one time. The authentication technique may include the separation and addition of the individual digits of one or more numerical codes to obtain a second value, e.g. 19704 would generate the number 21. In one embodiment, the numerical code may be on the surface or the interior of the dosage form, and the sum of the digits of the code may correspond to the amount or concentration of a chemical marker used to indicate the code. It may be desirable that the internal or external patterns or codes be scanned using a computer scanner, bar code reader, or other appropriate apparatus to capture the features of the pattern or code in sufficient resolution and detail to provide proper identification.

The sections above disclose a number of aspects of the present invention that may function alone or in combination in an effort to deter pharmaceutical counterfeiting. It is expected that combinations of one or more of the aspects listed above will be preferable in the practice of the present invention in that they offer multiple levels of protection against potential counterfeiting.

While specific embodiments of the various aspects of the present invention have been disclosed herein for descriptive purposes, a range of equivalent modifications or substitutions may be made that lie within the scope and spirit of the present invention, as recognized by those skilled in the art. Hence, the present invention should not be limited to the examples and discussion of the disclosure above, but instead the scope of the invention shall be determined entirely by the following claims.

What is claimed is:

1. A three-dimensionally printed dosage form comprising:
   a. a three-dimensionally printed solid matrix comprising a blend of at least one active ingredient and at least one inactive ingredient; and
   b. at least one or more chemical markers, wherein said one or more chemical markers define one or more internal three-dimensional patterns in said matrix that cannot be fully observed when the dosage form is intact and that may be used to authenticate the dosage form, wherein said one or more chemical markers is comprises dye, pigment, color-shift substance, UV-active substance, fluorescent substance, or another inactive pharmaceutical ingredient, wherein said one or more internal patterns includes logo, batch code, lettering, numbering, a dot pattern, or a bar code, and wherein the internal pattern is non-concentric or asymmetric.

2. The dosage form of claim 1, wherein one or more chemical markers is imperceptible to the naked eye.

3. The dosage form of claim 1, wherein one or more internal patterns is detectable just below the outer surface of the dosage form.

4. The dosage form of claim 1, wherein the numbering is separated into individual digits for subsequent addition to obtain a secondary value.

5. The dosage form of claim 1, wherein the number is a numerical code and the sum of the digits of the code corresponds to the amount of concentration of chemical marker used to indicate the code.

6. The dosage form of claim 1 further comprising an external feature used to identify, distinguish or authenticate a genuine dosage form from a counterfeit dosage form.

7. The dosage form of claim 6, wherein the external feature comprises a logo, specific regions with raised or lowered surface features, pattern of color, pattern of chemical marker, or a combination thereof.

8. The dosage form of claim 1, wherein one or more patterns constitutes three-dimensional arrangements that are non-concentric, asymmetrical or otherwise locally variable.

9. The dosage form of claim 1, wherein upon breaking or sectioning of the dosage form, one or more patterns is readily observable, requires exposure to a chemical or common substance for observation, requires use of analytical equipment for detection, or a combination thereof.

10. The dosage form of claim 1 further comprising one or more three-dimensionally printed fracture lines.

11. The dosage form of claim 10, wherein the dosage form is designed to break in one or more predetermined ways.

12. The dosage form of claim 11, wherein the dosage form is designed to break in one or more predetermined ways to expose said one or more patterns.

13. The dosage form of claim 12, wherein one or more patterns includes letters and numbers that lie along different axes of the same dosage form.

14. The dosage form of claim 13, wherein a three-dimensional pattern is designed to expose prespecified two-dimensional patterns on the exposed interior surface of the dosage form when the dosage form is broken or cut along specific axes of the dosage form.

15. The dosage form of claim 12, wherein one or more patterns includes a batch code.

16. The dosage form of claim 1, wherein the dosage form comprises interlocking pieces.

17. The dosage form of claim 1 further comprising one or more two-dimensional internal patterns of chemical marker.

18. The dosage form of claim 1 further comprising one or more two-dimensional external patterns of chemical marker.

19. The dosage form of claim 1 further comprising one or more additional chemical markers defining one or more external patterns or one or more internal patterns.

20. The dosage form of claim 1, wherein the dosage form comprises multiple internal patterns that are observable by breaking or sectioning the dosage form in different ways.

21. The dosage form of claim 1 comprising plural different chemical markers.

22. The dosage form of claim 1, wherein the chemical markers are present on the outer surface and interior of the dosage form.

* * * * *